March 21, 1961 W. FLEMER III Plant Pat. 2,038
THORNLESS HONEY LOCUST TREE
Filed Nov. 4, 1959
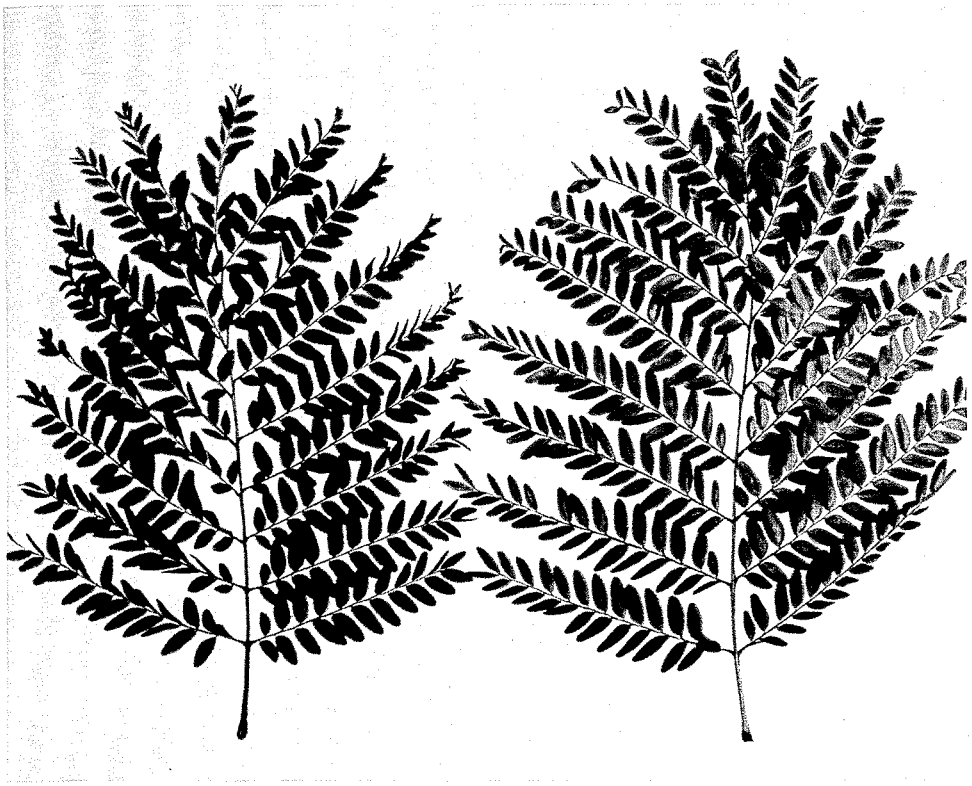
Inventor.
William Flemer, III.
By: Robb & Robb
Attorneys.

United States Patent Office

Plant Pat. 2,038
Patented Mar. 21, 1961

2,038

THORNLESS HONEY LOCUST TREE

William Flemer III, Princeton, N.J., assignor to Princeton Nurserymen's Research Associates, Princeton, N.J., a partnership Filed Nov. 4, 1959, Ser. No. 850,978

1 Claim. (Cl. 47—59)

The present invention relates to a new and distinct variety of thornless honey locust tree which was originated by me by crossing two unnamed and unpatented seedlings which are identified in my breeding records as variety #51–9 and #51–16, respectively, the former being the male parent, and the latter being the female parent.

The primary object of this breeding was to produce a new variety of honey locust which bears red leaves and which retains a red coloring throughout the growing season. In attempting to achieve this result, I selected two parent seedlings which exhibited reddish young growth, and on crossing these seedlings, I successfully achieved the result sought, which represents a completely new and unique "break" in honey locust colors, as evidenced by the fact that the young leaves initially come out with a brilliant red color, and although they gradually change to a dark bronze color as they mature, the foliage as a whole continues to present a definite red appearance because of the continuous succession of new leaves during the growing season.

Except for the foliage color distinction referred to above, which is enhanced and emphasized by the translucence of the leaflets, my new variety is not appreciably different from other thornless honey locusts, but because of its remarkable foliage of a shade and intensity heretofore unknown in thornless honey locusts, my new variety constitutes a valuable addition to the locust field, to the same extent as the unusual yellow variety known as "Sunburst" (Plant Patent No. 1,313).

Asexual reproduction of my new honey locust by budding (sometimes termed bud-grafting), as performed by me at my nursery in the township of Plainsboro, New Jersey, shows that the foregoing characteristics and distinctions come true to form and are established and transmitted through succeeding propagations.

The accompanying drawing shows typical specimens of the foliage of my new variety, with one view depicting the upper surface and the other view the lower surface thereof, as illustrated in color as nearly true as it is reasonably possible to make the same in a color illustration of this character.

The following is a detailed description of my new variety, with color terminology in accordance with the Munsell Color Chart, except where general color terms of ordinary dictionary significance are obvious:

Parentage: Seedling.
- *Male parent.*—An unnamed variety designated as #51–9.
- *Female parent.*—An unnamed variety designated as #51–16.

Propagation: Holds its distinguishing characteristics through succeeding propagations by budding.

Locality where grown and observed: Princeton, New Jersey.

Tree: Medium size; moderate grower; moderately drooping spreading habit; medium tall; medium slow growing; very hardy; not productive of fruit.
- *Head.*—Ovate.
- *Trunk.*—Slender. Bark—medium rough.
- *Branches.*—Slender; thin; moderate branching; no thorns produced. Bark—medium rough. Color—Reddish Brown, Plate 2.5 YR 2/4; definitely darker than any other honey locusts of which I am aware.
- *Lenticels.*—Abundant; small.

Foliage:
- *Leaves.*—Medium small; bipinnate; from 17 to 20 pinnae per leaf, and from 28 to 32 leaflets per pinna; average length from 28 to 34 cm.; average width from 29 to 35 cm.
- *Leaflets.*—Unequally cuneate-lanceolate; individual leaflets average length from 2.3 to 2.6 cm. and average width 9 or 10 mm.
- *Rachis.*—Glabrous and moderately grooved.
- *Color.*—Young leaves: upper surface—Bright Maroon Red, Plate 5.0 R 3/10; lower surface—Dull Maroon-Red, Plate 2.5 R 3/8. Old leaves: upper surface—Dark Bronze, Plate 7.5 R 2/2; lower surface—Dull Bronze-Green, Plate 7.5 Y 3/2.
- *Margin.*—Serrulate-undulate.
- *Petiole.*—Short; medium thick.
- *Glands.*—None.
- *Stipules.*—Produced on early leaves in growing season; from 2 to 2.25 cm. long.

Flower buds: Depressed; very small; globose, sparingly setose.

Flowers: Mid-Season, as compared with other varieties; medium size; medium abundance; only staminate flowers produced to date. Color—Pale Green-Yellow, Plate 5.0 Y 8/6.

Fruit: None produced to date.

I claim:

A new and distinct variety of thornless honey locust tree, substantially as herein shown and described, characterized particularly as to novelty by the distinctive translucent and bright red general color tonality of the foliage.

No references cited.